United States Patent
Quinn (10) Patent No.: US 7,323,347 B2
(45) Date of Patent: Jan. 29, 2008

(54) BIOSENSOR SURFACE STRUCTURES AND METHODS

(75) Inventor: John G. Quinn, Dallas, TX (US)

(73) Assignee: Sensata Technologies, Inc., Attleboro, MA (US)

( * ) Notice: Subject to any disclaimer, the term of this patent is extended or adjusted under 35 U.S.C. 154(b) by 337 days.

(21) Appl. No.: 11/140,414

(22) Filed: May 27, 2005

(65) Prior Publication Data

US 2006/0134695 A1 Jun. 22, 2006

Related U.S. Application Data

(60) Provisional application No. 60/575,664, filed on May 27, 2004.

(51) Int. Cl.
*G01N 33/543* (2006.01)

(52) U.S. Cl. .................. 436/518; 385/12; 385/129; 385/130; 385/131; 422/82.05; 422/82.11; 435/287.2; 435/288.7; 435/808; 436/164; 436/524; 436/525; 436/805

(58) Field of Classification Search ............. 385/12, 385/129, 130, 131; 422/82.05, 82.11; 435/287.2, 435/288.7, 808; 436/164, 518, 524, 525, 436/805
See application file for complete search history.

(56) References Cited

U.S. PATENT DOCUMENTS

| | | | | |
|---|---|---|---|---|
| 4,844,613 A * | 7/1989 | Batchelder et al. | ......... | 356/318 |
| 4,877,747 A * | 10/1989 | Stewart | ............... | 436/525 |
| 5,242,828 A * | 9/1993 | Bergstrom et al. | ....... | 435/287.1 |
| 5,492,840 A * | 2/1996 | Malmqvist et al. | ......... | 436/518 |
| 5,629,213 A * | 5/1997 | Kornguth et al. | ........... | 436/518 |
| 5,633,724 A * | 5/1997 | King et al. | ............... | 356/445 |

* cited by examiner

*Primary Examiner*—Christopher L. Chin
(74) *Attorney, Agent, or Firm*—Russell E. Baumann (57) ABSTRACT

A biosensor surface with a low density of ligand-carrying tether molecules on a base layer. Also, surface plasmon resonance (SPR) devices have the biosensor surface attached to a thin gold layer with backside angle-spread incident radiation for resonance excitation and reflective detection.

8 Claims, 3 Drawing Sheets

BIOSENSOR SURFACE STRUCTURES AND METHODS

CROSS REFERENCE TO RELATED APPLICATIONS

This application claims priority from provisional patent application No.: 60/575,664, filed May 27, 2004. The following copending applications disclose related subject matter and have a common assignee with the present application: application Ser. Nos. 10/152,745 and 10/152,760, both filed May 22, 2002, and Ser. No. 10/799,283, filed Mar. 12, 2004.

BACKGROUND OF THE INVENTION

The present invention relates to analytic chemical measurements, and more particularly to biosensor surfaces and related methods.

Analytical instruments such as biosensors are well established as a means of recording the progress of biomolecular interactions in real time. Biosensors are analytical instruments that employ a variety of transduction technologies in order to detect interactions between biomolecules. A particularly effective evanescent field based technology, known as surface plasmon resonance (SPR), exploits the behavior of light upon reflection from a gold-coated optical substrate.

SPR is an optical technique that enables real-time monitoring of changes in the refractive index of a thin film close to the sensing surface. The evanescent field decays exponentially from the gold surface and falls to one third of its maximum intensity at approximately 300 nm from the surface. Hence, the SPR technique is sensitive to surface refractive index changes and is almost completely insensitive to refractive index variations which occur more than 300 nm from the surface. An integrally-formed miniature SPR transducer has previously been described in U.S. Pat. No. 5,912,456. In this device a photodiode array (PDA) simply records the intensity of the reflected light, from an light emitting diode (LED), over a range of angles. Refractive index changes within the penetration depth of the evanescent field give rise to corresponding angular changes in the position of the SPR reflectance minimum. This change in resonance angle is followed by tracking the change in the PDA pixel position of the reflectance minimum. A minimum tracking algorithm is employed to continuously monitor the position of this minimum as it traverses the photodiode array and the pixel position is then related to a refractive index value. The current configuration of this device possesses three SPR active sensing regions per sensor enabling multichannel operation with real-time reference subtraction. Alternative configurations can allow as many as 100 or more SPR sensing regions.

The delivery of samples to the SPR active sensing regions is made possible by creating flow channels that cover the active sensing regions. Each flow channel possesses an inlet and outlet to allow for the flow of buffer, or samples, over the SPR active sensing regions.

In order to provide specificity to SPR, a biomolecule is typically immobilized near the gold surface. This immobilized biomolecule is referred to as a ligand. The immobilized ligand usually possesses binding specificity for another biomolecule contained in a sample, this other biomolecule is referred to as the analyte. The strength of this binding is given by the affinity constant (K) which is simply the ratio of the association rate constant ($k_a$) divided by the dissociation rate constant ($k_d$). It is possible to measure these constants because an SPR-based biosensor records the progress of binding and dissociation events in real time. To a large degree the performance of the biosensor is dictated by the properties of the surface preparation. Since the specificity of SPR-based biosensors is dictated by the choice of ligand to be immobilized at the sensing surface, it is possible to detect a wide range of analytes by simply choosing the appropriate ligand. However it is important that the ligand is immobilized in such a way as to retain its solution phase characteristics of solubility, accessibility, and analyte binding activity.

There are several properties that an attachment layer, with immobilized biomolecules, must possess in order to ensure optimal biosensor performance. These properties may vary depending on the requirement of a particular application. The following is a list summarizing the properties of an SPR biosensor surface that should be considered.

(1) Attachment Stability. The surface should possess ligands linked via stable bonds, such as covalent bonds, to ensure that leaching of the ligand from the surface during an application does not occur. It is important that the analyte binding capacity of the surface remains constant throughout the duration of a measurement or set of measurements.

(2) Three-Dimensional Accessibility. The ligand is best linked in such a way as to be fully accessible to the analyte. When the ligand is directly linked to a planar surface, for example, then three-dimensional access is not possible. Such a situation can alter the activity of the ligand and can thereby interfere with the extraction of accurate kinetic data.

(3) Capacity. Some biosensing applications require a large amount of ligand to be held by the surface. Examples of such applications include direct binding assays to determine the concentration of analyte down to very low levels. Some biosensing applications require low to medium levels of bound ligand to be held by the surface. Kinetics studies, equilibrium studies and competitive assays fall into this category because very high levels of ligand can impose mass transport limited conditions and other hindrances.

(4) Resistance to Non-Specific Binding (NSB). Binding of sample components other than analyte to the biosensing surface is referred to as non-specific binding. The performance of any biosensing technology can be reduced by the occurrence of NSB and so the NSB properties of the surface immobilization chemistry are important.

Hydrophobic sites at the surface commonly give rise to an increase in non-specific binding because physisorption of proteins to surfaces is known to be mediated by hydrophobic interactions. Also, an excess of charged groups also generally increases the probability of non-specific binding. For example, some proteins possess a net positive charge at neutral pH and will tend to associate with negatively charged surfaces.

(5) Uniform Distribution of Binding Sites. The surface should provide a uniform distribution of ligand across the sensing surface. But for highly surface-sensitive techniques such as SPR, it is also important to maintain a uniform distribution of immobilized ligands within the evanescent field penetration depth (i.e., above the surface). A non-uniform distribution in this dimension will also create problems for kinetic models since it is very difficult to account for such heterogeneity, and the analysis, therefore, becomes less robust. Specifically, typical kinetic binding models assume that analyte binds to all available binding sites homogenously and not as an inward moving analyte binding front.

(6) Monovalent Linkage. Multiple linkages between the ligand and the surface can cause steric hindrance by obstructing analyte binding sites. Thus, multivalent linkage can cause a fraction of immobilized ligand to be rendered less accessible than others. This will not only lower surface capacity, but more importantly will create a population of differentially accessible analyte binding sites. Meaningful kinetic data cannot be recorded under these conditions. Ligand binding sites must be fully accessible and this is best accomplished by ensuring a single linkage with the surface.

(7) Diffusion Limitations. Transport of analyte to the immobilized ligand at the sensing surface is a function of the diffusion rate of the analyte, the liquid flow rate, and the dimensions of the flow cell. High mass-transport rates typically yield more accurate kinetic data. However, mass transport of analyte may be distorted by the presence of three-dimensional structures, such as hydrogels, at the sensing surface. The analyte diffusion rate decreases within the hydrogel, thus compromising kinetic analyses.

(8) Chemical Resistance. The gold film should be insulated from the aqueous environment using a chemically-resistant thin film. Analytes are sometimes poorly soluble in aqueous buffers and the addition of solvents such as DMSO, or DMF, often enables solublization. Therefore that thin film must tolerate short-term exposure to such solutions. Resistance to common buffers, weak acids, weak bases, surfactants, and denaturants (e.g. 6M guandine-HCl, pH 2.0) is also desired.

SPR technologies have been available commercially for over a decade, and a considerable body of knowledge now exists as evidenced by thousands of peer-reviewed journal articles. A review of the literature indicates that kinetic analysis remains the mainstay of SPR applications, but other applications, such as concentration measurement, epitope mapping, interaction dynamics, ligand fishing, and affinity analysis are also common. Since the properties of the film that allows for ligand attachment at the biosensing surface is a critical component for all these applications, and because different applications have different surface demands, many approaches to surface attachment chemistries have been developed.

The most basic approach that has been applied to SPR involves directly attaching ligands to the gold surface and without the benefit of an intermediate film. While this approach is simple enough, its limitations are numerous. First of all, since this is a planar two-dimensional surface, the maximum amount of ligand that can be attached is a monolayer (approximately 3000 RU for an antibody, for example, where 1 RU is equivalent to a $1 \times 10^{-6}$ change in refractive index or a surface coverage of approximately 1 pg/mm$^2$). In the case where the ligand is a protein, which is most common, most of the protein attached in this manner will denature on the gold surface thereby rendering it inactive. And even those proteins that manage to remain active will suffer from steric hindrance because this binding is taking place directly on a planar surface. This will further reduce the ability of the analyte to access the active binding regions of the ligand. So, this technique produces limited loading and poor activity due to denaturation and steric hindrance.

U.S. Pat. No. 5,242,828 describes an improvement over direct ligand attachment to the gold by construction of a self-assembled monolayer (SAM) of alkane thiolates that chemisorb onto a gold surface to from a pseudo-crystalline monolayer as an intermediate layer for biosensing. Here the thiol end of the molecule binds to the gold and the film organizes itself into a self-assembled monolayer. This type of film provides an effective insulating layer that both protects the gold from harsh reagents and also protects the ligand from the denaturing effects of direct binding to a gold surface. In addition, the non-thiol end of the alkane thiol can be functionalized with hydrophilic groups to promote biocompatibility and also with reactive groups to allow for covalent attachment. The practice of applying alkane thiols to gold surfaces uniformly can be tricky because any contamination, which forms readily on the gold upon exposure to air, will result in non-uniform SAM formation.

A modification of the alkane thoiolate SAM approach is described in U.S. Pat. No. 5,436,161. This describes the grafting of a porous matrix (e.g., hydrogel) onto the alkanethiolated surface, where that hydrogel contains both charged groups for preconcentrating oppositely charged ligand molecules into the gel and reactive groups that allow for covalent attachment of ligand molecules to the gel. This matrix coating is typically ~100 nm thick, and due to its three dimensional nature, allows for up to ten times the binding capacity of a normal planar surface coating. The use of hydrogels on the sensing surface was first proposed by Liedberg et al. in 1983. The most popular hydrogel matrix used today is a carboxymethylated dextran-based hydrogel. Its high density of carboxyl groups throughout the three-dimensional gel is suspected of causing non-specific binding when used with some biological systems. In addition, the use of a high-density anchoring matrix in a biosensor also creates the potential for several well-documented matrix-related artifacts in kinetic studies as described below.

Random grafting of the dextran polymer, at any point along the chain, to the surface is unavoidable in the fabrication of hydrogel-based coatings. Non-uniform ligand binding with poor penetration of analyte to ligands located close to the surface may occur due to an increased density of polymer chains closer to the surface. This effect becomes more pronounced for high molecular weight analytes. Concerns related to the increasing density of the gel near the surface, have been noted. Indeed, D. Hall, Use of Optical Biosensors for the Study of Mechanistically Concerted Surface Adsorption Processes, 288 Anal. Biochem. 109-125 (2001), concluded that "As the existence of possible gel-induced partition and transport limitations cannot, in consideration, be divorced from the external transport processes as well as from consideration of the fundamental properties of the interacting system (intrinsic chemical reaction kinetics, ligate and ligand size, the concentration of ligate and immobilized receptor), the provision of clear guidelines for experimentation is difficult". Also, the potential kinetic artifacts related to a variable density of ligand throughout the depth of the evanescent field are to be considered.

In a carboxymethylated dextran coating, for example, both the negative charge and reactive groups are distributed throughout the hydrogel since there is no way to specifically position them, and while this results in a highly effective preconcentration and immobilization of ligand, this process also allows the ligand to be bound by more than one linkage site and this is quite problematic. In fact it is likely that as many as three or four linkages are possible. Löfács at al., Dextran Modified Gold Surfaces for Surface Plasmon Resonance Sensors: Immuno-reactivity of Immobilized Antibodies and Antibody-Surface Interaction Studies, 1 Colloids and Surfaces B, Biointerfaces, 83-89 (1993), found lower specific binding activities of ligands that were immobilized onto the carboxymethylated hydrogel via random amine coupling. This was attributed to multipoint attachment to the hydrogel. In cases where the occurrence of multipoint attachment was reduced (accomplished by using very high density ligand coupling), the analyte binding activity was found to be as high as 75%. But since low immobilization levels are required for most applications, this tendency to form multiple cross-linkages is quite problematic for hydrogel matrices due to their inherently high densities.

Furthermore, because there is charge throughout the hydrogel, and because the presence of charge affects the gel's structure, there is a tendency for the hydrogel to cause shifts in the baseline during biosensor measurements. These shifts result from the fact that changes in pH or ionic strength tend to change the density of charged hydrogels, and such density fluctuations give rise to undesirable shifts in the baseline response.

So, while the hydrogel matrix described in U.S. Pat. No. 5,436,161 does enable very high ligand loading, limitations of this method include analyte transport difficulties, multivalent attachment, ligand gradients and baseline instability.

Other work using carboxymethylated hydrogels as anchoring layers for biosensor surfaces includes Piehler et al., A High Density Poly(ethylene glycol) Polymer Brush for Immobilization on Glass Type Surfaces. 15 Biosensors & Bioelectronics, 473-481 (2000), which concluded, "These layers reduce non-specific binding, but proportionally interfere with the binding event and can also affect the sensitivity of the transducer". Consequently, Piehler et al. replaced the dextran hydrogel with densely packed polyethylene glycol (PEG) chains grafted onto a planar surface. Similar to the results obtained using the technique of U.S. Pat. No. 5,242,828 non-specific binding was also found to be extremely low, but only a monolayer of ligand could be bound.

In addition, Piehler at al. had previously found that PEG chains did not effectively prevent non-specific binding when grafted at less than maximal densities. This is in agreement with the conclusions of Sheth et al., Measurements of Attractive Forces between Proteins and End-grafted Poly (ethylene glycol) Chains. 94 Proc. Natl. Acad. Sci., 8399-8402 (1997), working on attractive forces between PEG and proteins, which concluded " . . . the activation energy for protein polymer adhesion increased with the polymer grafting density. Denser layers thereby increase not only the diffusional barrier but also the energy required to form attractive protein-polymer bonds". Simply put, the conclusion was that the higher the density of the PEG layers, the more effective the film became at resisting non-specific binding.

Thus, current SPR sensors have problems related to their surface coatings. Planar two-dimensional surfaces allow only for monolayer ligand surface coverage. Matrix-based hydrogels allow for up to ten times higher ligand loading, but they also impart artifacts in kinetic data related to limited transport through the gel, ligand density variations, charge induced density changes, and multivalent attachment.

SUMMARY OF THE INVENTION

The present invention provides a biosensor surface with a base layer optionally combined with tether molecules for immobilizing ligands. Preferred embodiment base layers are on gold layers which support plasmon resonance useful in preferred embodiment SPR devices.

This has advantages including true three-dimensional analyte binding to ligands arising from the low density of tether molecules.

DETAILED DESCRIPTION OF THE PREFERRED EMBODIMENTS

1. Overview

Figure 1:
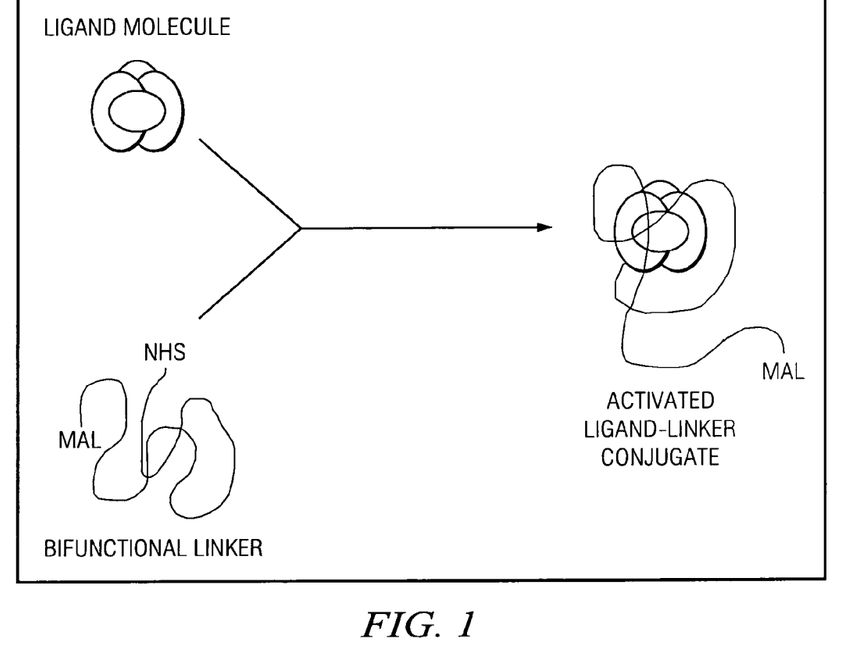
FIGS. 1-3 show fabrication steps for a preferred embodiment biosensor tether molecule attachment to a base layer.
Figure 2:
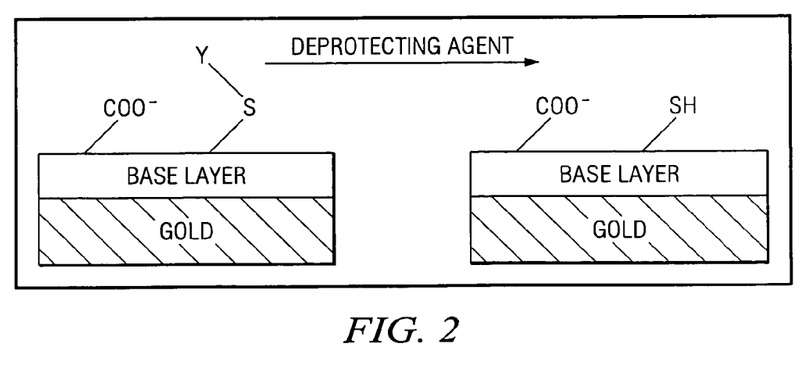
Figure 3:
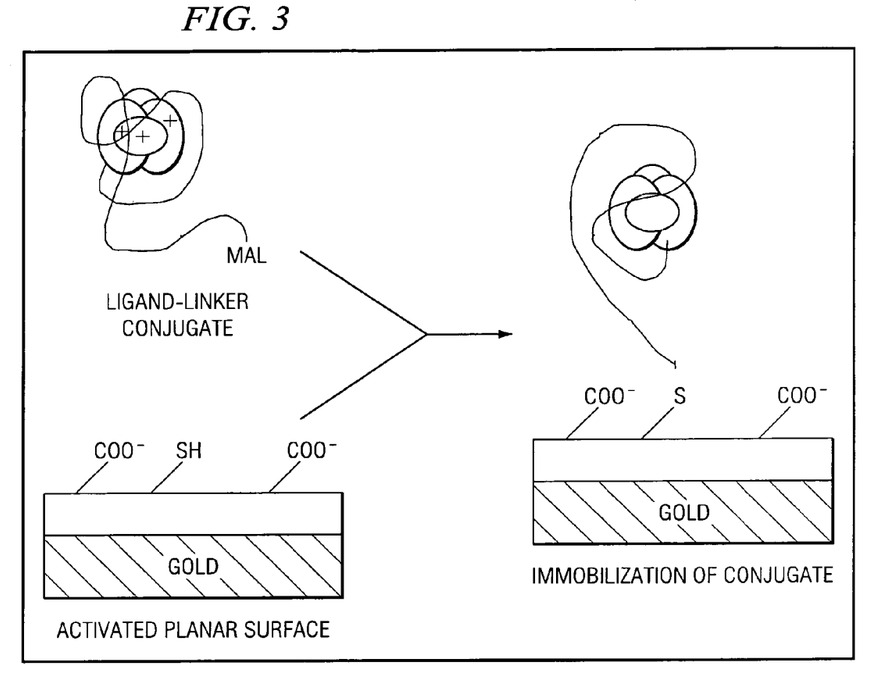
Figure 4:
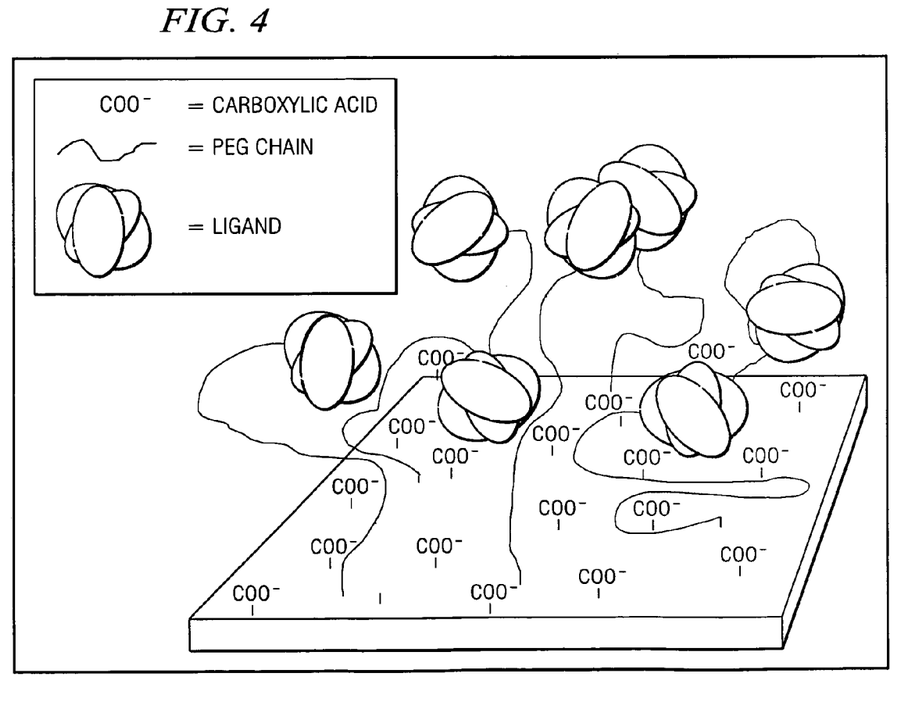
FIG. 4 is a perspective view of a preferred embodiment biosensor surface.

Preferred embodiment biosensors and sensing methods conjugate ligands to tether (linker, spacer) molecules which are then immobilized onto a base layer adsorbed to a gold (SPR metal) surface. Alternative preferred embodiments immobilize the ligands directly to a base layer without tethers. The base layer is hydrophilic and contains charged groups to allow for preconcentration of ligand during the immobilization process. Long, uncharged flexible tether molecules have a low surface density on the base layer. These long uncharged tether molecules preferably use covalent attachment to both the ligand and the base layer surface so that attachment is stable. These tether molecules are long enough and are at low enough density to allow both (a) the ligand relief from the surface and thereby full analyte accessibility to the ligand and (b) greater ligand loading than is possible for a purely planar surface, all without creating analyte mass transport and other artifacts that are commonly seen in dense matrices containing ligands. FIGS. 1-3 illustrate the preferred embodiment tether molecule ligand attachment and immobilization on the base layer. FIG. 4 is a perspective view illustrating the low density of tether molecules on the base layer.

The alternative preferred embodiments with direct ligand immobilization on the base layer use the base layer as in FIG. 2 and the ligands as in FIG. 1 but without the tethers. The resulting immobilization differs from FIG. 3 in that the tether molecules are omitted and the ligands directly bond to the thio groups.

Figure 5:
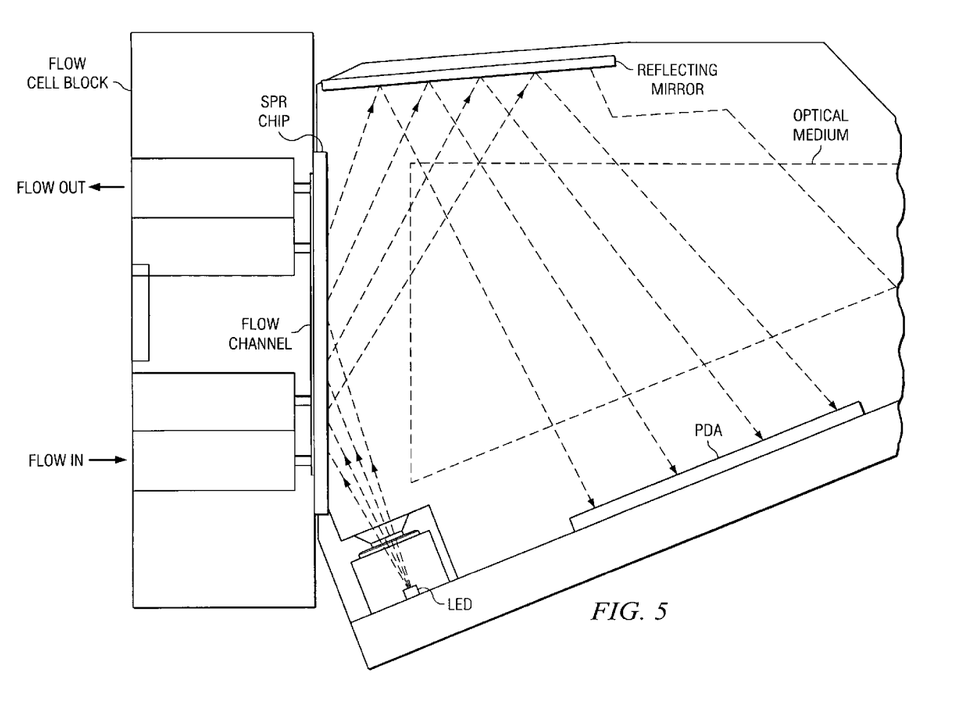
FIG. 5 illustrates a preferred embodiment SPR device in cross-sectional elevation view.

FIG. 5 shows in cross-sectional elevation view a complete preferred embodiment SPR device which includes a preferred embodiment biosensor surface structure as part of the SPR chip.

The tether molecules should define a spatial region with a thickness of at most about 400 nm; this ensures analyte captured by ligands will be within the region of substantial evanescent field and thus affect the refractive index. For roughly linear tether molecules such as bifunctional poly (ethylene glycol) (PEG) with a ligand at one end and a reactive group for attachment to the base layer at the other end, the tether molecule lengths (when linearly extended) should be in the range of 2-400 nm.

2. Preferred Embodiment Characteristics

Preferred embodiment base layers have characteristics as follows.

(a) Charge should be present at the planar surface to allow for preconcentration of an oppositely-charged ligand. This charge must be restricted to the planar surface, rather than extending above the surface for the following reasons. First, during assays, non-specific binding in sample buffers (i.e., high ionic strength) via electrostatic interactions will be minimized because the charge is confined to the planar surface and therefore electrostatic field penetration depth is less than 1 nm. In fact, in this case, a repulsive force will be generated by an osmotic pressure gradient that results from the accumulation of counter-ions at the surface (i.e., electrical dipole layer), thus further preventing non-specific binding. So, confining the charge to the surface allows preconcentration of ligand (to enable efficient immobilization) and the generation of an osmotic repulsive force (to prevent non-specific binding) depending on the buffer conditions (i.e., pH and ionic strength). And the latter cannot be accomplished when charge is based in the region above the surface.

(b) The surface should be planar and also be hydrophilic in order to further prevent non-specific binding which is largely mediated via hydrophobic interactions.

(c) In addition, there should be reactive groups at the base layer surface to allow for direct attachment of the ligands, or for tether-ligand conjugates, to the surface.

Preferred embodiment tether molecules have the following properties:

(a) Uncharged: The tether molecule should be uncharged so that only the planar surface holds charge. Charge that is allowed to propagate above the surface can cause non-specific binding during assays as well as charge induced artifacts associated with the buffer's ionic strength and detergent content and must therefore be avoided.

(b) Length: The tether molecule should be long enough to provide the ligand relief from the surface thus allowing full analyte access and greater than monolayer surface loading of ligand. Thus a tether molecule length of 3-400 nm will be suitable. The vast majority of analytes will vary in size from 0.1-50 nm in diameter, assuming a globular structure.

Uncharged PEG chains at low densities tend to adopt a random coil structure on a planar surface. The average end position of a PEG chain grafted to the planar surface at low densities is proportional to the Flory radius, Rf, the average coil dimension in solution:

$$R_f = aN^{0.6}$$

where a=length of ethylene oxide monomer=0.341 nm
N=number of monomer units in polymer This estimate implies that 3.5 kDa (N=79), 10 kDa (N=227), and 20 kDa (N=454) PEGs will have Flory radii of 4.7 nm, 8.8 nm, and 13.4 nm, respectively. However the maximum extension of each chain will be 27 nm, 77 nm, and 155 nm, respectively. Electrostatic repulsion between adjacent ligands will ensure separation of the tethered ligands, but the maximum distance of any ligand from the surface is limited to the maximum extension of the chosen PEG chain.

The tether chain length should allow extension of the immobilized ligand within 30 nm of the surface in order to accommodate binding of high molecular weight analytes without causing overcrowding effects. Therefore, a PEG chain with a molecular linear length in the range from 3 nm to 400 nm is suitable with a preferred length in the range from 7 nm to 150 nm.

(c) Flexibility: Charge preconcentration onto a planar carboxylated surface results in the accumulation of a high concentration of protein at the surface. However, a monolayer equivalent of this preconcentrated mass is capable of covalent binding to a planar charged surface due to crowding effects. In contrast, the use of highly mobile, flexible tether molecules enables a larger portion of the preconcentrated mass to be coupled. For example, direct immobilization of an antibody onto a carboxylated surface, without the use of tether molecules, typically results in the immobilization of approximately 1500 RU In comparison, antibody immobilization responses of over 4,000 RU are possible using the preferred embodiment methods employing immobilization of tether-ligand conjugate molecules on a charged planar surface. The high performance of this surface results from supporting the ligand in the aqueous medium using flexible tether molecules as opposed to binding it directly to a solid planar surface. However, it has been demonstrated that the binding activity and accessibility of ligands immobilized directly to our base layer is similar to those obtained using the preferred embodiment tether-ligand conjugate method. This is most likely due to osmotic repulsion and limited cross-linking at the surface. Higher capacity is expected using the tether-ligand conjugate method particularly when using branched tethers. However, it may be preferable to use direct immobilization of the ligand when considering mass transport effects as the diffusion of the immobilized ligand is zero.

(d) Monovalent Attachment: Ideally, the tether molecule should only have one reactive group on each end, where one end is designed to bind only to the ligand and the other end is designed to bind only to the surface. This will allow conditions to exist where each ligand is attached to only one tether molecule. In the case where the tether and ligand are conjugated prior to surface attachment, this is accomplished by controlling the stoichiometry of the conjugation reaction so that the final product is a 1:1 conjugate of ligand molecules to tether molecules. In the case where the tether is attached to the surface prior to ligand conjugation, 1:1 coupling is accomplished by limiting the surface coverage of the tether molecule so that it is unlikely that one ligand can attach to more than one tether molecule.

(e) Hydrophilic: The tether molecules should also be inherently hydrophilic to minimize the occurrence of non-specific binding to the tethers, themselves.

In short the preferred embodiment characteristics are as follows:

The base layer is thin compared to the probe depth of the evanescent field. Its thickness should therefore not exceed 20 nm, but is preferably 1-10 nm. Its surface is approximately planar so that its charge cannot extend above the surface, thereby minimizing nonspecific binding. The base layer should be substantially impenetrable and should not swell in water so that baseline drift due to conformational changes under changing buffer conditions does not occur.

A tether molecule should have reactive groups only at its two ends. The reactive group at one end is chosen to react with the ligand and the other is chosen to react with the base layer surface. This specifically supports monovalent attachment. The tether molecules are to be long and flexible to provide the ligand relief from the charged planar base layer. This relief enables both three-dimensional access by the analyte as well as a degree of three-dimensional loading.

The tether molecule can first be attached to the ligand and then that conjugate attached to the base layer surface. The ligand-tether conjugate is attached to the surface, an average ratio of ligand to tether of 1:1 (monovalency) is readily achieved by controlling the reaction stoichiometry. A branched tether may support attachment of multiple ligands and hence increase binding capacity.

In either case, in order to accelerate ligand attachment to the surface, it is useful to employ a charged planar surface to preconcentrate ligand that possesses an opposite charge. And so, the preferred embodiments have a planar charged surface for preconcentrating and attaching ligand molecules or ligand-tether molecule conjugates to the surface.

3. Preferred Embodiment Immobilization with Tethering

A preferred embodiment method first links the ligands to preferred embodiment tether molecules (NHS-PEG-MAL) in a 1:1 ratio, and then immobilizes the ligand-tether conjugates to a preferred embodiment base layer. FIGS. 1-3 illustrate the following conjugation and immobilization process.

1) Dissolve protein (ligand) to be immobilized in 5 mM phosphate buffer, pH 7.4, at a concentration of 5-10 mg/ml.
2) Add a 5 fold molar excess of bifunctional polyethylene glycol (NHS-PEG-MAL) with the PEG chain of length about 27 nm (N=79); the MAL terminal group is maleimide which will covalently bond to the base layer in step 4), and the NHS terminal group is N-hydroxy succinimide which reacts with free amines of the ligand. The MAL and NHS are ether-linked to the PEG ends. Incubate at room temperature for 30 min. This has been empirically shown to provide a 1:1 ratio between conjugated PEG and ligand, but can vary depending on reaction conditions. The NHS end reacts preferentially; see FIG. 1.
3) Activate the base layer surface to generate free thiols. See FIG. 2.
4) Dilute the protein conjugate from step 2) to 50 ug/ml in 5 mM acetate buffer (pH is set below the pI of the ligand) and inject over the planar carboxylated surface from step 3). Allow to react with the surface for 1-60 min, depending on the desired immobilization level. The carboxylates provide negative charge for ligand concentration and the maleimide groups react with the free thiols from step 3); see FIG. 3.
5) Cap excess free thiols using N-ethylmaleimide in acetate buffer pH 5.0.

FIG. 4 is a perspective view where it is understood that the tether molecules (and ligands) are not confined but, rather, move about with the most common configuration being a somewhat coiled up PEG chain of size comporting with its Flory radius (~5 nm). This movement allows analyte unhindered access to the ligands.

4. Preferred Embodiments of Base Layers

The base layer may be comprised of any of a variety of thin, non-swellable films that will form both a protective coating on the gold surface and one which can be derivatized for a low-density of tether molecule attachment.

One preferred embodiment base layer is a cross-linked protein film. For example, a base layer can be built up from a monolayer of bovine serum albumin (BSA) adsorbed plus thiol-bonded to the gold surface by reacting available amine groups (of lysine residues in BSA) with various short bifunctional molecules (e.g. bisxoirane) to yield a surface of mostly carboxylate groups together with thiol groups. These carboxylate groups provide the charge, and the thiol groups provide sites for direct attachment of the ligand or tether-ligand conjugates. The thiols can be protected as disulfides; and the fraction of thiols compared to carboxylates may be controlled by relative concentrations of bifunctional molecules in a solution. Optionally the surface may be constructed without disulfide or thiol groups and in this case biomolecules may be immobilized by activation of a small fraction of the available carboxylic groups thereby providing reactive groups for covalent coupling and charge for the concentration of oppositely charged biomolecules.

Other preferred embodiment base layers include the family of organic films composed of polyolefins, or teflon, which can be superior to self-assembled alkane thiols at protecting gold because they can be designed to resist a broader variety of chemicals, including oxidants, acids, bases, in addition to physical resistance to temperature, abrasion, and desorption (or delamination).

In all cases, the thickness of the base layer should be minimized in order to support biomolecules close to the gold surface where the evanescent field is strongest. A thickness from 0.5 to 10 nm is desirable. The base layer may be composed of any non-water-swellable polymer or mixture of polymers to form a film that may be crystalline, pseudo crystalline or amorphous. Polymers in the form of colloidal suspensions are easily physisorbed as a monolayer onto the gold surface. The thickness of the resulting film is easily controlled by simply choosing particles of an appropriate diameter. More sophisticated methods for deposition of base layers include chemical vapor deposition, plasma polymerization of monomers in the gas phase, spin-coating, dip-coating and spray coating.

Some examples of suitable polymers are poly(vinyl chloride), poly(ethylene), poly(propylene), poly(tetrafluroreth-ylene). A large number of organic polymers and copolymers are suitable. Amphiphilic organic polymers such as peptides, proteins (described above), and diblock copolymers may be used. In fact, protein is a good example of an amphiphilic molecule capable of interacting strongly with the metal surface via hydrophobic interactions and the exposed hydrophilic groups orientate towards the aqueous phase. These hydrophilic groups (e.g. hydroxyl, thiol, carboxyl, amino, and imidazole) may be easily derivatized with, or without, plasma activation.

An exemplary preferred embodiment base layer can be prepared with the following steps.

1) A protein solution is prepared in water where the molecule size is in the order of 2-50 nm.
2) A gold surface (on a glass substrate) is prepared by prolonged exposure to an $H_2$ plasma inside a radio-frequency glow discharge reactor.
3) The gold surface is then submerged in the protein solution until a monlolayer of the protein is deposited by physisorption onto the gold (e.g., 10 minutes).
4) The gold surface is then rinsed with excess water and annealed at 100-100° C. to 170° C. for 0.5 hours to 24 hours.
5) Epoxy-group activate the monolayer by covalent coupling of a monolayer of a bisoxirane, said epoxy-group activated monolayer is of a thickness of <1 nm; and the bisoxirane preferably is butanedioldiglycidyl ether.
6) React a fraction of the epoxy groups with thioglycolate to incorporate carboxyl groups, and hydrolyze the remaining fraction of epoxy groups to yield hydroxyl groups.
7) Binding ligands to the monolayer; the carboxyl groups provide charge attraction and a small fraction are derivatized to reactive functionalities for covalent attachment of ligand molecules. The hydroxyls provide optional binding sites but their primary function is to prevent non-specific binding of biomolecules to the functionalized surface.

A second exemplary preferred embodiment base layer can be prepared with the following steps.

1) A non-ionic colloidal suspension of Teflon particles is prepared in water where the particle size is in the order of 2-50 nm.
2) A gold surface (on a glass substrate) is prepared by prolonged exposure to an $H_2$ plasma inside a radio-frequency glow discharge reactor.
3) The gold surface is then submerged in the colloidal solution until a monlolayer of the polymeric particles is deposited by physisorption onto the gold (e.g., 10 minutes).

4) The gold surface is then rinsed with excess water and annealed at 100-100° C. to 170° C. for 0.5 hours to 24 hours.
5) The inert teflon coated gold surface is activated by exposure to an $O_2$ plasma inside a radio-frequency glow discharge reactor. The power setting and exposure time are optimized to allow the incorporation of reactive oxygen species, such as peroxy radical and oxygen coatining groups such as hydroxyl groups and carboxy groups, while minimizing removal of any material by etching.
6) Epoxy-group activate the monolayer by covalent coupling of a monolayer of a bisoxirane, said epoxy-group activated monolayer is of a thickness of <1 nm; and the bisoxirane preferably is butanedioldiglycidyl ether.
7) React a fraction of the epoxy groups with thioglycolate to incorporate carboxyl groups, and hydrolyze the remaining fraction of epoxy groups to yield hydroxyl groups.
8) Binding ligands to the monolayer; the carboxyl groups provide charge attraction and a small fraction are derivatized to reactive functionalities for covalent attachment of ligand molecules. The hydroxyls provide optional binding sites but their primary function is to prevent non-specific binding of biomolecules to the functionalized surface.

5. Preferred Embodiment Tether Molecules

PEGs make excellent tether molecules since their ends can be outfitted with functional groups and they can also inherently have no charge along their length. A mixture of PEGs of various lengths could be used as can branched PEGs. Other options include non-charged hydrophilic polymers such as poly(ethylene oxide), poly(propylene oxide), poly(vinyl alcohol), poly(acrylic acid) and poly(acrylamide).

6. Preferred Embodiment Tether Functional Groups

PEG-based hetero-bifunctional tethers are preferred. These are long unbranched PEG chains terminated on both ends with reactive groups. These reactive groups can be chosen from a group consisting of epoxy, maleimide, hydrazide, succinimidyl, halogen, carbonylimidazole, aldehyde, vinlysulfone, tresylate, tosylate, and pyridyl sulfide. The linkage of PEG bifunctional tethers to molecules, or surfaces, is referred to as PEGylation. Roberts et al., Chemistry for Peptide and Protein Pegylation, 54 Advanced Drug Delivery Reviews 459-476 (2002), reviews the application of PEGylation for the modification of pharmaco-kinetic properties of therapeutic agents. The flexibility of the PEG backbone chain and its dynamic interaction with the aqueous environment prevent biomolecules from adsorbing to the polymer surface. Therefore PEG is an ideal choice for preventing non-specific binding.

7. Preferred Embodiment Immobilization Method with Tether.

The foregoing preferred embodiment ligand immobilization method described the pre-preparation of the tether-ligand conjugate in a 1:1 molar ratio. That tether-ligand conjugate was then pre-concentrated onto a carboxylated surface that was first derivatized to possess free thiols. The free maleimide end groups of the tether molecule reacted with surface thiols to form irreversible thioether bonds even at low pH. Free thiols were capped by exposure to N-ethylmaleimide.

Pretreatment of the ligand with a thiolating agent such as 2-iminothiolane, to incorporate an average of one free thiol per ligand molecule, enables the more stable, bis(maleimide)-PEG (MAL-PEG-MAL) to be used in place of NHS-PEG-MAL. The ligand may also be PEGylated to give a free reactive hydrazide group. The preconcentrated conjugate will form hydrazone bonds when reacted with aldehyde groups on the planar surface. Reduction of the hydrazone bond yields a stable hydrazide bond. Ligands that possess free thiols are more conveniently immobilized using methods as described above.

8. Preferred Embodiment Immobilization Method without Tether.

In an alternative preferred embodiment the ligand molecule is pre-concentrated onto the charged surface and directly immobilized via a covalent bond formed between the reactive groups of the base layer and endogenous functional groups contained on the ligand. This eliminates the need to use a tether and molecules immobilized in this way have been shown to possess similar characteristics to that expected in solution phase. This is in contrast with results obtained using other planar base layer structures. The base layer structure has been optimized to support the immobilization of tether-ligand conjugates and direct immobilization of the ligand. It is believed that the presence of a charged hydrophilic monolayer at the surface, a low number of ligand-base layer cross-links, an osmotic repulsion force all contribute to a biocompatible environment that resists non-specific binding and preserves the binding activity, and accessibility, of the immobilized ligand.

This preferred embodiment is in contrast to other planar immobilization methods where denatuartion of the ligand and analyte steric hindrance are highly problematic. Such denaturation has been associated with the tendency of proteins to physisorb onto solid surfaces. The preferred embodiment based layer resists physisorption of ligand molecules thereby preserving its biological activity.

What is claimed is:

1. A process of fabricating a sensing surface, comprising the steps of:
   (a) forming a base layer, said base layer is composed of a monolayer of colloidal particles chosen from a group consisting of proteins, peptides, colloidal PTFE particles, colloidal polyethylene particles, colloidal polypropylene particles wherein said particles are of a diameter in the range of 0.5 nm to 100 nm;
   (b) epoxy-group activating said monolayer by covalent coupling of a monolayer of a bisoxirane, said epoxy-group activated monolayer is of a thickness not to exceed 1 nm;
   (c) reacting a fraction of said epoxy groups with thioglycolate to incorporate carboxyl groups and the remaining fraction are hydrolyzed to yield hydroxyl groups; and
   (d) binding ligands to said monolayer.

2. The method of claim 1 wherein said monolayer of colloidal particles is activated by exposure to an oxygen gas plasma for the covalent incorporation of hydroxyl groups and peroxide groups wherein said monolayer of bisoxirane is covalently bound via said reactive oxygen containing groups.

3. The method of claim 1 wherein said colloidal particles are proteins or peptides and wherein functional groups contained on surface of said protein or peptide molecules, are chemically derivatized to yield reactive thiol groups.

4. The method of claim 3 where said derivatization of said functional groups is accomplished using the thiolating reagents 2-iminothiolane or N-acetylhomocysteine thiolactone.

5. The method of claim 1 where said bisoxirane is butanedioldiglycidyl ether.

6. The method of claim 1 wherein carboxylic groups and hydroxyl groups are incorporated onto said epoxy activated monolayer by reaction with sodium thioglycolate under alkaline aqueous conditions.

7. The method of claim 1, wherein said ligands possess one or more tether molecules of a length exceeding 1 nm wherein said tether molecules contain at least one reactive group that forms an irreversible covalent bond with said base layer reactive groups.

8. An SPR biosensor, comprising:
(a) a base layer bound to a plasmon resonance capable metal film, said base layer composed of a monolayer of colloidal particles chosen from a group consisting of proteins, peptides, colloidal PTFE particles, colloidal polyethylene particles, and colloidal polypropylene particles, said particles are of a diameter in the range of 0.5 nm to 100 nm;
(b) ligands bound to said base layer; and
(c) an optical source and reflection detector optically coupled to said metal film;
(d) wherein said monolayer of particles is epoxy group activated by covalent coupling of a monolayer of a bisoxirane, said epoxy-activated monolayer is of a thickness not to exceed 1 nm.

* * * * *